United States Patent [19]

Adachi et al.

[11] Patent Number: 4,774,331

[45] Date of Patent: Sep. 27, 1988

[54] PROCESS FOR ORTHO-CYANATION OF PHENOLS OR PHENYLAMINES

[75] Inventors: Makoto Adachi, Nara; Hiromu Matsumura; Tsutomu Sugasawa, both of Hyogo, all of Japan

[73] Assignee: Shionogi & Co., Ltd., Osaka, Japan

[21] Appl. No.: 87,885

[22] Filed: Aug. 21, 1987

[30] Foreign Application Priority Data

Aug. 22, 1986 [JP] Japan .................................. 61-197701

[51] Int. Cl.$^4$ ............................................. C07C 43/08
[52] U.S. Cl. ......................................... 544/35; 544/51; 544/52; 544/102; 544/105; 544/347; 544/353; 540/605; 540/609; 546/165; 546/223; 546/230; 548/444; 548/491; 548/557; 548/561; 558/376
[58] Field of Search ................... 558/376; 544/35, 51, 544/52, 105, 102, 347, 353; 540/605, 609; 546/165, 230, 223; 548/444, 491, 557, 561

[56] References Cited

PUBLICATIONS

G. R. Bedford et al., "A Convenient Preparation . . . ," 1959, pp. 1633–1634.
I. B. Johns et al., "Coordination Compounds . . . ," vol. 27, 7/24/61, pp. 592–594.
Houben et al., Ber., vol. 63 (1930) pp. 2464–2473.

*Primary Examiner*—Richard L. Raymond
*Attorney, Agent, or Firm*—Birch, Stewart, Kolasch & Birch

[57] ABSTRACT

A process for ortho-cyanation of phenols or phenylamines which comprises reacting a phenyl compound having hydroxy or optionally substituted amino or cyclic amino, of which ortho position is vacant, with trichloroacetonitrile, $C_1$–$C_5$ alkyl thiocyanate or $C_6$–$C_{12}$ aryl thiocyanate in the presence of a boron trihalide and treating the resultant product with an alkali is provided, and said process is useful in the synthesis of intermediates for medicinals or pesticides.

16 Claims, No Drawings

PROCESS FOR ORTHO-CYANATION OF PHENOLS OR PHENYLAMINES

BACKGROUND OF THE INVENTION

The present invention relates to a process for ortho-cyanation of phenols or phenylamines. More particularly, this invention is directed to a process for ortho-cyanation of phenols or phenylamines which have been found to be particularly useful in the synthesis of intermediates for medicinals and pesticides.

As this kind of prior arts, the undermentioned reactions are known.

(a) J. Houben and W. Fischer, Ber., 63 2464 (1930)

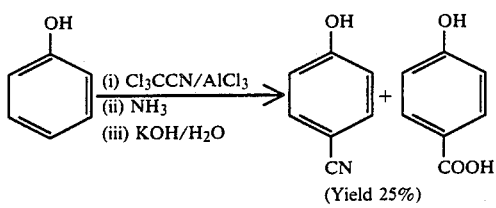

(Yield 25%)

This reaction can introduce a cyano group at the paraposition of the hydroxy group, whereby no ortho-substituted product is obtained.

(b) I. B. Johns et al., J. Org. Chem., 27 592 (1962)

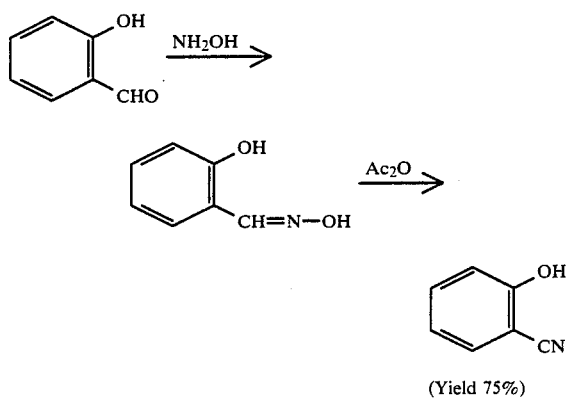

(Yield 75%)

(c) G. R. Bedford et al., J. Chem. Soc., 1633 (1959)

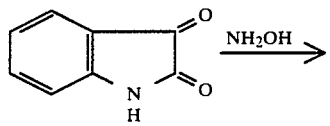

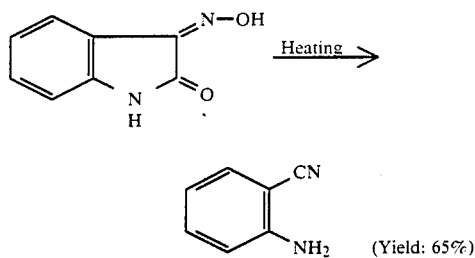

(Yield: 65%)

In these conventional reactions a satisfactory yield is not always achieved, and o-substituted benzonitrile derivatives having another desirable substituent at any desired position are not obtained.

SUMMARY OF THE INVENTION

According to the present invention there is provided a process for the ortho-cyanation of phenols or phenylamines which comprises reacting a phenyl compound having a hydroxy or optionally substituted amino or cyclic amino, of which the ortho position is vacant, with trichloroacetonitrile, $C_1$–$C_5$ alkyl thiocyanate or $C_6$–$C_{12}$ aryl thiocyanate in the presence of a boron trihalogenide and treating the resultant product with an alkali.

The said reaction is summarized by the undermentioned scheme.

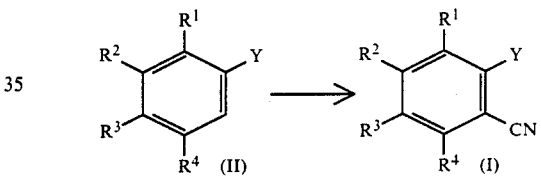

(wherein $R^1$, $R^2$, $R^3$ and $R^4$ each is hydrogen, halogen, $C_1$–$C_5$ alkyl, $C_1$–$C_5$ alkoxy, $C_1$–$C_5$ alkylthio, $C_6$–$C_{12}$ aryloxy, $C_7$–$C_{15}$ aralkyl, $C_7$–$C_{15}$ aralkoxy or $C_1$–$C_{10}$ acylamino, or $R^1$ and $R^2$) or ($R^2$ and $R^3$) each taken together form a condensed benzene ring optionally substituted by halogen, $C_1$–$C_5$ alkyl or $C_1$–$C_5$ alkoxy, Y is hydroxy, amino or NHR, and R is $C_1$–$C_5$ alkyl, $C_7$–$C_{15}$ aralkyl, $C_6$–$C_{12}$ aryl, N-(methyl- or benzyl-substituted)aza($C_3$–$C_7$)cycloalkyl or N-(methyl- or benzyl-substituted)aza($C_3$–$C_7$)cycloalkyl-methyl).

The said phenyl compound (II) consists of two types, A type and B type.

A type

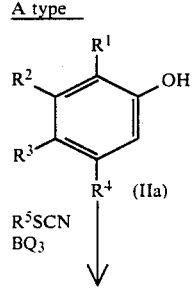

$R^5$SCN
$BQ_3$ weak base

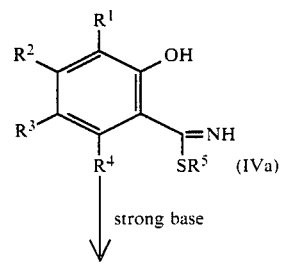

strong base

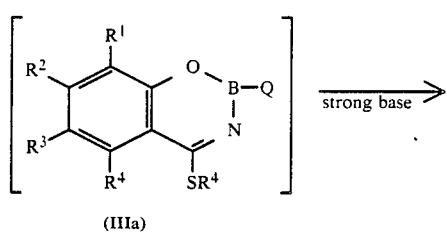

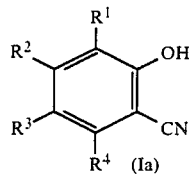

(IIIa)

B type

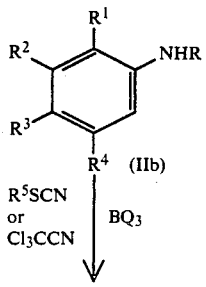

(IIb)

R⁵SCN
or
Cl₃CCN

BQ₃ weak
base
(when Z = SR⁵)

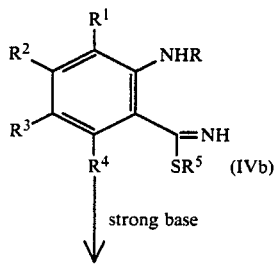

(IVb)

strong base (i) weak base
(when Z = CCl₃) or
(ii) strong base
(when Z = SR⁵)

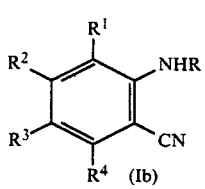

(IIIb)

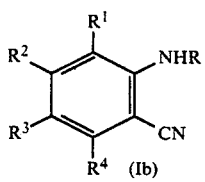

(Ib)

(wherein $R^1$, $R^2$, $R^3$, $R^4$ and R each has the same meaning as defined above; Q is halogen (Cl or Br), Z is CCl₃ or SR⁵, and R⁵ is $C_1$–$C_5$ alkyl or $C_6$–$C_{12}$ aryl).

Further, B type (IIb) includes additionally C type (IIc) and D type (IId). When R and $R^1$ of the B type (IIb) taken together form a 5- or 6-membered heterocycle, the reactions of these compounds are illustrated as follows:

C type

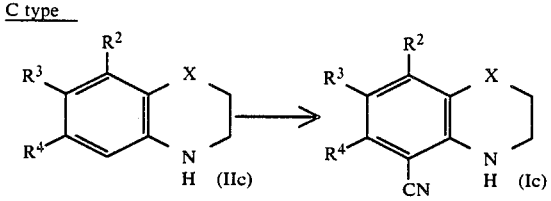

(IIc) → (Ic)

D type

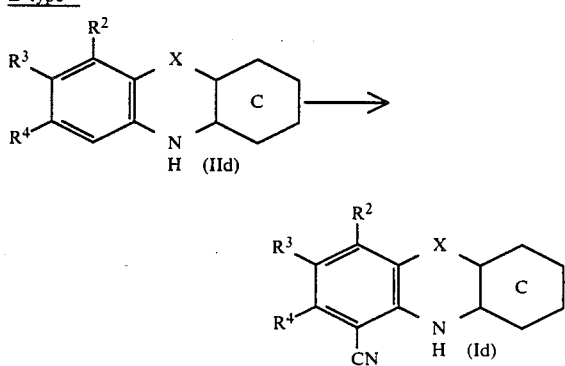

(IId) → (Id)

(wherein C ring is benzene ring optionally substituted by halogen, $C_1$–$C_5$ alkyl or $C_1$–$C_5$ alkoxy, X is a single bond O, S or N(methyl), and $R^2$, $R^3$ and $R^4$ each has the same meaning as defined above).

The terms used in the above definition will be illustratively explained below.

The term "$C_1$–$C_5$ alkyl" herein employed refers to a straight or branched saturated aliphatic hydrocarbon radical such as methyl, ethyl, n-propyl, n-butyl, isobutyl, sec-butyl, tertbutyl, n-pentyl and neo-pentyl.

The term "halogen" represents fluorine, chlorine, bromine and iodine.

The term "$C_1$–$C_5$ alkoxy" represents methoxy, ethoxy, n-propoxy, isopropoxy, n-butoxy, isobutoxy, sec-butoxy, tert-butoxy, n-pentyloxy and sec-pentyloxy.

The term "$C_1$–$C_5$ alkylthio" represents methylthio, ethylthio, propylthio, isopropylthio, butylthio, pentylthio and iso-pentylthio.

The term "$C_6$–$C_{12}$ aryloxy" includes phenoxy, tolyloxy and naphthoxy.

The term "$C_7$–$C_{15}$ aralkyl" includes benzyl, phenethyl, phenylpropyl, phenylbutyl, naphthylmethyl and naphthylpropyl.

The term "$C_7$–$C_{15}$ aralkoxy" includes benzyloxy, phenethyloxy, phenylpropyloxy, phenylbutyloxy and naphthylmethoxy.

The term "$C_1$–$C_{10}$ acylamino" includes formylamino, acetylamino, propionylamino, butyrylamino, benzoylamino, phenylacetylamino and phenylbutyrylamino.

The term "$C_6$–$C_{12}$ aryl" means phenyl and naphthyl.

The term "$C_3$–$C_7$ cycloalkyl" in the definition of N(methyl- or benzyl-substituted)aza($C_3$–$C_7$ cycloalkyl) means cyclopropyl, cyclobutyl, cyclopentyl, cyclohexyl and cycloheptyl.

Moreover, the alkyl, alkoxy, aryl, aryloxy, aralkyl and aralkoxy above mentioned may be optionally substituted by alkyl, alkoxy or halogen.

The boron trihalogenide used in this process refers to boron trichloride or boron tribromide.

The thiocyanates usable as one of the other reagents includes alkyl thiocyanates and aryl thiocyanates of which hydrocarbon groups may have one or more members selected from alkyl group, alkoxy group and halogen.

As the thiocyanates used herein, methyl thiocyanate, ethyl thiocyanate, propyl thiocyanate, butyl thiocyanate and phenyl thiocyanate are exemplified.

The process of the present invention comprises reacting a phenyl compound (II) having hydroxy or optionally substituted amino or cyclic amino, of which the ortho position is vacant, with trichloroacetonitrile, $C_1$-$C_5$ alkyl thiocyanate or $C_6$-$C_{12}$ aryl thiocyanate in the presence of a boron trihalogenide and treating the resultant boron compound (IIIa) or (IIIb) with an alkali. More particularly, this reaction will be explained below in detail.

A type

The phenol (II) is allowed to react with a thiocyanate in the presence of a boron trihalogenide to give an intermediate compound (IIIa), and the boron compound (IIIa) is then treated with a strong base to give a 2-cyanophenol (Ia). Alternatively, the 2-cyanophenol (Ia) can be prepared via the thiocarboxyimidic acid ester (IVa) by stepwise hydrolysis. Thus, IIIa is at first treated with a weak base to give IVa, which is then treated with a strong base to give the 2-cyanophenol (Ia).

The reaction of the phenol (II) with a thiocyanate is performed by heating in an inert solvent such as methylene chloride, 1,2-dichloroethane, benzene, toluene, xylene or the like at a temperature from room temperature (1°–30° C.) to about the boiling point of the solvent used. The reaction proceeds smoothly, but the yield increases by adding an appropriate Lewis acid (e.g. aluminium chloride, stannic chloride, titanium tetrachloride, etc.). For preventing side reactions, further the reaction can be performed in an inert atmosphere such as nitrogen or argon.

When the boron compound (IIIa) is hydrolyzed with a weak base such as sodium carbonate, potassium carbonate, sodium hydrogencarbonate, sodium acetate or potassium phosphate at room temperature (1°–30° C.), the thiocarboxyimidic acid ester (IVa) is obtained, which is then hydrolyzed with a strong base such as sodium hydroxide or potassium hydroxide to give the product (Ia). When the boron compound (IIIa) is treated with a strong base, the objective 2-cyanophenol (Ia) is directly prepared. The hydrolysis can be performed in an aqueous or alcoholic medium at room temperature (0°–30° C.) or under heating (50°–80° C.) in a conventional manner.

B type

The phenylamine (IIb) is allowed to react with a thiocyanate or trichloroacetonitrile in the presence of a boron trihalogenide (boron trichloride or boron tribromide) to give the intermediary boron compound (IIIb). The reaction of IIb with trichloroacetonitrile can be performed as above described in the reaction with a thiocyanate. The boron compound (IIIb) (Z=CCl$_3$) is treated with a weak base to give the product (Ib), and IIIB (Z=SR$^5$) is treated with a strong base to give the product (Ib) but treated with a weak base to give the further intermediate (IVb), which is then treated with a strong base to give the product (Ib). The hydrolysis is performed in a conventional manner.

C type and D type

The cyclic amines (IIc) and (IId) are allowed to react with a thiocyanate or trichloroacetonitrile quite similarly as in the reaction of the phenylamine (IIb).

Presently preferred and practical embodiments of the process of the present invention are illustratively shown in the following working examples, which do not limit the technical scope of the present invention.

The abbreviations used in Examples and Tables have the following meanings.

| | | |
|---|---|---|
| Me = methyl | Et = ethyl | n-Bu = n-butyl |
| Ph = phenyl | OMe = methoxy | SMe = methylthio |
| CH$_2$Ph = benzyl | TL = toluene | DM = methylene chloride |
| DE = 1,2-dichloroethane | | HCl = hydrochloric acid |

EXAMPLE 1

To 6 ml of a solution of 2.02M of boron trichloride in 1,2-dichloroethane were added a solution of 941 mg of phenol in 10 ml of 1,2-dichloroethane, 0.82 ml of methyl thiocyanate and 1.33 g of aluminium chloride under ice-cooling. After dissolving aluminium chloride with stirring at room temperature, the mixture was heated at 80° C. on an oil bath for 3 hr. After cooling, the reaction solution is poured into 33 ml of 4N aqueous sodium hydroxide and stirred at 75°–80° C. for 30 min. on an oil bath. The aqueous layer was washed with methylene chloride, acidified with 25 ml of 6N HCl and extracted with ether. Then, the ether layer was washed with 2N aqueous sodium carbonate, dried over anhydrous magnesium sulfate and concentrated to recover 39 mg of phenol. On the other hand, the sodium carbonate layer was acidified with 6N HCl and extracted with ether. The ether layer was dried over anhydrous magnesium sulfate and evaporated to remove the solvent. The crystalline residue (1.13 g) was recrystallized from methylene chloride-petroleum ether, whereby 1.002 g of 2-cyanophenol was obtained as colorless crystals melting at 97°–98° C.

Yield: 84%

EXAMPLE 2-12

Using the undermentioned starting material (IIa), the reaction was performed in the same manner as in Example 1, whereby the corresponding objective compounds (Ia) were obtained.

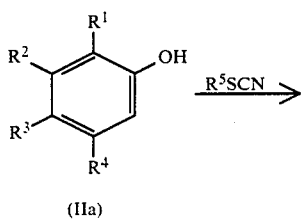

(IIa)

-continued

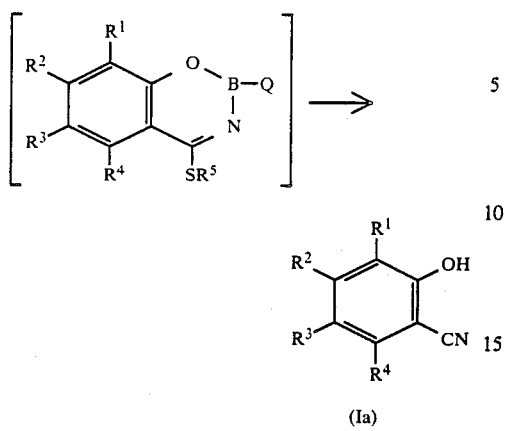

The reaction was performed with aluminium chloride as a Lewis acid at a temperature of 80° C. in a solvent of 1,2-dichloroethane. The results were shown in Table 1.

TABLE 1

| Ex. No. | R¹ | R² | R³ | R⁴ | R⁵ | Time (hr) | M.P. (°C.) | Yield (%) |
|---|---|---|---|---|---|---|---|---|
| 2 | H | H | H | H | Et | 3 | 96–97 | 74 |
| 3 | H | H | H | H | n-Bu | 3 | 96–97 | 68 |
| 4 | Me | H | H | H | Me | 3 | 83–84 | 85 |
| 5 | H | Me | H | H | Me | 3 | 126–127 | 82 |
| 6 | H | H | Me | H | Me | 3 | 100–101 | 91 |
| 7 | H | Me | Me | H | Me | 3 | 204–206 | 89 |
| 8 | Cl | H | H | H | Me | 64 | 115–116 | 28 |
| 9 | H | Cl | H | H | Me | 16 | 159–160 | 84 |
| 10 | H | H | Cl | H | Me | 40 | 167–169 | 43 |
| 11 | Cl | Cl | H | H | Me | 40 | 144–145 | 32 |
| 12 | H | Cl | H | Cl | Me | 40 | 211–212 | 10 |

EXAMPLE 13

To a solution of 1.13 ml of boron tribromide in 6 ml of 1,2-dichloroethane were added a solution of 941 mg of phenol in 10 ml of 1,2-dichloroethane, 0.82 ml of methyl thiocyanate and 1.33 g of aluminium chloride under ice-cooling. After dissolving aluminium chloride with stirring at room temperature, the mixture was heated at 80° C. on an oil bath for 3 hr. After cooling, the reaction solution was poured into 33 ml of 4N aqueous sodium hydroxide and stirred at 75°–80° C. for 30 min. on an oil bath. After washing with methylene chloride, the aqueous layer was acidified with 25 ml of 6N HCl and extracted with ether. The ether layer was extracted with 2N aqueous sodium carbonate, dried over anhydrous magnesium sulfate and concentrated to recover 147 mg of phenol. On the other hand, the sodium carbonate layer was acidified with 6N HCl, extracted with ether, and the ether layer was dried over anhydrous magnesium sulfate and concentrated. The residue was recrystallized from methylene chloride-petroleum ether to give 943 mg of 2-cyanophenol as white crystals melting at 97°–98° C.

Yield: 79%

EXAMPLE 14

To 5 ml of a solution of 2.02M of boron trichloride in benzene were added a solution of 1.24 g of 4-methoxyphenol in 12 ml of benzene, 0.82 ml of methyl thiocyanate and 1.33 g of aluminium chloride. After stirring at room temperature for 16 hr., the reaction mixture was poured into 30 ml of 4N aqueous sodium hydroxide and stirred at 75°–78° C. on an oil bath for 30 min. After cooling, the aqueous layer was washed with ethylene chloride, acidified with 6N HCl and extracted with ether. After drying the ether layer over anhydrous magnesium sulfate, the solvent was distilled off. The crystalline residue was recrystallized from ether-petroleum ether to give 1.24 g of 2-hydroxy-4-methoxybenzonitrile as white crystals melting at 176°–177° C.

Yield: 83%

EXAMPLE 15–20

Using the undermentioned starting material (IIa), the reaction was performed in the same manner as in Example 14, whereby the corresponding objective compounds (Ia) were obtained. The results were shown in Table 2.

TABLE 2

| Ex. No. | R¹ | R² | R³ | R⁴ | solvent | Time (hr) | m.p. (°C.) | Yield (%) |
|---|---|---|---|---|---|---|---|---|
| 15 | OMe | H | H | H | DE | 16 | 47–48 | 17 |
| 16 | H | H | OMe | H | DE | 16 | 140–141 | 66 |
| 17 | H | OMe | OMe | H | DE | 16 | 148–150 | 82 |
| 18 | H | OMe | H | OMe | DE | 16 | 206–207 | 86 |
| 19 | H | H | SMe | H | DE | 24 | 148–149 | 21 |
| 20 | Et | H | H | OMe | DMe | 16 | 125–126 | 78 |

EXAMPLE 21

To 6 ml of a solution of 2.02M of boron trichloride in 1,2-dichloroethane were added a solution of 1.44 g of β-naphthol in 30 ml of 1,2-dichloroethane, 0.82 ml of methyl thiocyanate and 1.33 g of aluminium chloride under ice-cooling. After stirring at room temperature for 3 hr., the reaction mixture was poured into 33 ml of 4N aqueous NaOH and stirred at 75°–78° C. on an oil bath for 30 min. The reaction solution was mixed with 30 ml of 6N HCl and extracted with ether. After drying the ether layer over anhydrous magnesium sulfate, the solvent was distilled off. The residue was recrystallized from ether-benzene to yield 1.49 g of 1-cyano-2-naphthol as crystals melting at 160°–161° C.

Yield: 88%

EXAMPLE 22

To 6 ml of a solution of 2.02M of boron trichloride in 1,2-dichloroethane were added a solution of 1.44 g of α-naphthol in 30 ml of 1,2-dichloroethane, 0.82 ml of methyl thiocyanate and 1.33 g of aluminium chloride under ice-cooling. After stirring at room temperature for 3 hr., the reaction mixture was poured into 33 ml of 4N aqueous NaOH and stirred at 75°–78° C. on an oil bath for 30 min. After cooling the aqueous layer was washed with methylene chloride, acidified with 25 ml of 6N HCl and extracted with ether. After drying the ether layer over anhydrous magnesium sulfate, the solvent was distilled off. The residue (1.51 g) was purified on a column of 30 g of silica gel. Then 1.26 g of the eluate with 10% ethyl acetate-methylene chloride was recrystallized from ether-petroleum ether to give 1.04 g of 2-cyano-1-naphthol as crystals melting at 182°–183° C.

Yield: 62%

EXAMPLE 23

To 6 ml of a solution of 2M of boron trichloride in 1,2-dichloroethane were added a solution of 941 mg of phenol in 10 ml of 1,2-dichloroethane, 0.82 ml of methyl thiocyanate and 1.33 g of aluminium chloride under ice-cooling. After dissolving aluminium chloride with stirring at room temperature, the mixture was heated at 80° C. on an oil bath for 3 hr. After cooling, the reaction solution was poured into 66 ml of 2N aqueous Na₂CO₃ and stirred for 15 min. To the mixture were added 50 ml of ether and 7 g of Hi-Flo Super-Cell, and aluminium hydroxide was filtered off. The mixture was extracted with ether. After drying the ether layer over anhydrous magnesium sulfate, the solvent was distilled off. The residue (1.43 g) was purified on a Lobar column. After recrystallization from ether-petroleum ether, the eluate with 5% ethyl acetate-methylene chloride gave 1.27 g of 2-hydroxybenzenethiocarboxyimidic acid methyl ester as yellow crystals melting at 45°–46° C. Yield: 76%

EXAMPLE 24–28

Using the undermentioned starting material (IIa), the reaction was performed in the same manner as in Example 23, whereby the corresponding objective intermediates (IVa) were obtained.

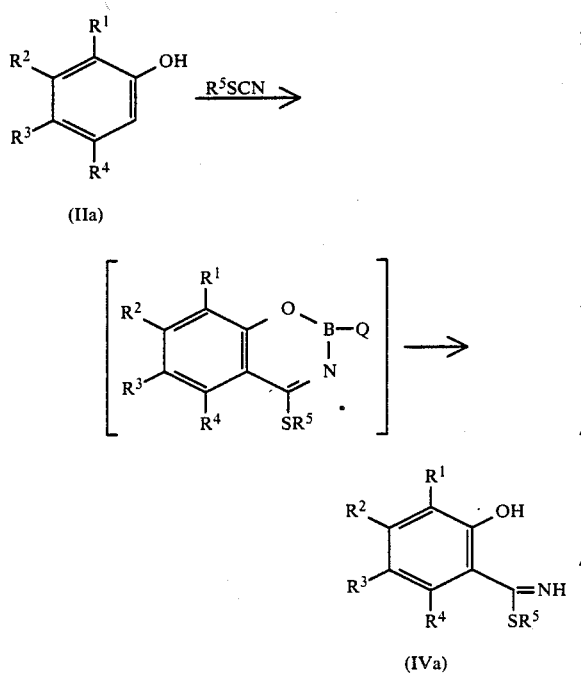

The reaction was performed with aluminium chloride as a Lewis acid in a solvent of 1,2-dichloroethane at a temperature of 80° C. The results were shown in Table 3.

TABLE 3

| Ex. No. | $R^1$ | $R^2$ | $R^3$ | $R^4$ | $R^5$ | Time (hr) | m.p. (°C.) | Yield (%) |
|---|---|---|---|---|---|---|---|---|
| 24 | Me | H | H | H | Me | 3 | 39–40 | 69 |
| 25 | H | Me | H | H | Me | 3 | 62–63 | 65 |
| 26 | H | H | Me | H | Me | 3 | 58–59 | 79 |
| 27 | H | Me | Me | H | Me | 3 | 109–110 | 57 |
| 28 | H | Cl | H | H | Et | 3 | 75–76 | 36 |

EXAMPLE 29

To 5 ml of a solution of 2M of boron trichloride in 1,2-dichloroethane were added a solution of 1.24 g of 4-methoxyphenol in 12 ml of 1,2-dichloroethane, 0.82 ml of methyl thiocyanate and 1.33 g of aluminium chloride under ice-cooling. After stirring at room temperature for 16 hr., the mixture was poured into 66 ml of 2N aqueous Na₂CO₃ and stirred for 15 min. To the mixture were added 50 ml of ether and 7 g of Hi-Flo Super-Cell, and aluminium hydroxide was filtered off. Then the filtrate was extracted with ether. The ether layer was dried over anhydrous magnesium sulfate, and evaporated to dryness. The residue (1.60 g) was purified on a Lobar column. The eluate with 5% ethyl acetate-methylene chloride was evaporated and the residue was recrystallized from ether-n-hexane to give 0.993 g of 2-hydroxy-5-methoxybenzenethiocarboxyimidic acid methyl ester as orange crystals melting at 66°–67° C.

Yield: 50%

Anal Calcd (%) for C₉H₁₁O₂NS: C, 54.80; H, 5.62; N, 7.10; S, 16.27; Found (%): C, 54.67; H, 5.56; N, 7.18; S, 16.25.

IR (CHCl₃): 3352 cm⁻¹

EXAMPLE 30–33

Using the undermentioned starting material (IIa), the reaction was performed in the same manner as in Example 29, whereby the corresponding objective intermediates (IVa) were obtained.

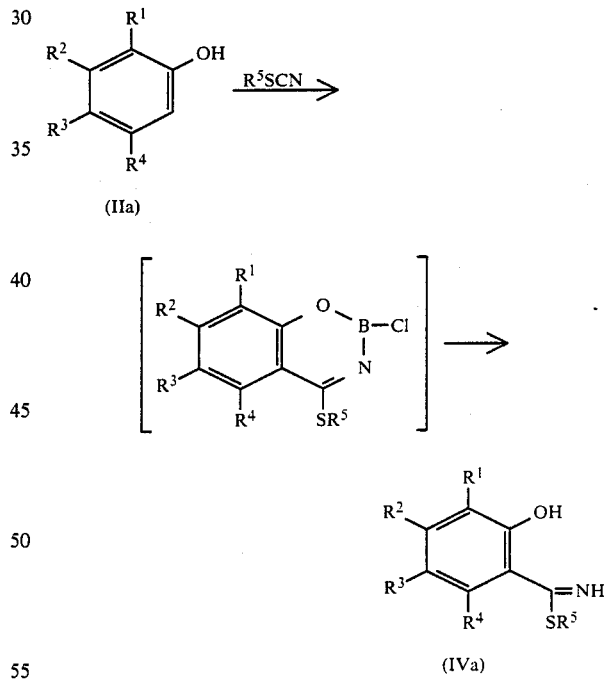

The reaction was performed with aluminium chloride as a Lewis acid at room temperature. The results were shown in Table 4.

TABLE 4

| Ex. No. | $R^1$ | $R^2$ | $R^3$ | $R^4$ | $R^5$ | solvent | Time (hr) | m.p. (°C.) | Yield (%) |
|---|---|---|---|---|---|---|---|---|---|
| 30 | H | OMe | H | H | Me | BN | 16 | 121–122 | 36 |
| 31 | H | OMe | OMe | H | Me | DE | 16 | 152–153 | 39 |
| 32 | H | OMe | H | OMe | n-Bu | DE | 16 | 94–95 | 48 |
| 33 | H | H | SMe | H | Me | DE | 24 | 91–92 | 11 |

EXAMPLE 34

To 6 ml of a solution of 2M of boron trichloride in 1,2-dichloroethane were added a solution of 1.44 g of β-naphthol in 30 ml of 1,2-dichloroethane, 0.82 ml of methyl thiocyanate and 1.33 g of aluminium chloride under ice-cooling. After stirring at room temperature for 3 hr., the reaction mixture was poured into 66 ml of 2N aqueous $Na_2CO_3$ and stirred for 15 min. The mixture was treated with 50 ml of methylene chloride and 7 g of Hi-Flo Super-Cell, and aluminium hydroxide was filtered off. The filtrate was extracted with methylene chloride. After drying the methylene chloride layer over anhydrous magnesium sulfate, the solvent was distilled off. The residue (2.14 g) was purified on a Lobar column. The eluate with 30% acetonitrile-methylene chloride was evaporated and the residue was recrystallized from methylene chloride-ether to give 1.81 g of 2-hydroxy-1-naphthalenethiocarboxyimidic acid methyl ester as crystals melting at 126°–127° C.

Yield: 83%

Anal Calcd (%) for $C_{12}H_{11}ONS$: C, 66.33; H, 5.10; N, 6.45; S, 14.76; Found (%): C, 66.36; H, 4.99; N, 6.42; S, 14.71.

IR (Nujol): 3272 $cm^{-1}$

EXAMPLE 35

To 6 ml of a solution of 2M of boron trichloride in 1,2-dichloroethane were added a solution of 1.44 g of α-naphthol in 30 ml of 1,2-dichloroethane, 0.82 ml of methyl thiocyanate and 1.33 g of aluminum chloride under ice-cooling. After stirring at room temperature for 5 hr., the reaction mixture was poured into 66 ml of 2N aqueous $Na_2CO_3$ and stirred for 15 min. The mixture was treated with 100 ml of methylene chloride and 7 g of Hi-Flo Super-Cell, and aluminium hydroxide was filtered off. The filtrate was extracted with methylene chloride. After drying the methylene chloride layer over anhydrous magnesium sulfate, the solvent was distilled off. The residue (1.52 g) was purified on a Lobar column. The eluate with 15% acetonitrile-methylene chloride was evaporated and the residue was recrystallized from acetonitrile—ether to give 1.02 g of 1-hydroxy-2-naphthalenethiocarboxyimidic acid methyl ester as crystals melting at 191°–193° C.

Yield: 47%

Anal Calcd. (%) for $C_{12}H_{11}ONS$: C, 66.33; H, 5.10; N, 6.45; S, 14.76; Found (%): C, 66.37; H, 5.04; N, 6.32; S, 14.69.

IR (Nujol): 3205 $cm^{-1}$.

EXAMPLE 36

2-Hydroxybenzenethiocarboxyimidic acid ethyl ester (1.34 g) was added to 1N NaOH (15 ml) and the mixture was stirred at 75°–78° C. on an oil bath for 30 min. After washing with methylene chloride, the aqueous layer was acidified with 3 ml of 6N HCl and extracted with ether. After drying the ether layer over anhydrous magnesium sulfate, the solvent was distilled off. The residue (0.78 g) was recrystallized from methylene chrloride-petroleum ether to give 0.703 g of 2-cyanophenol as white crystals melting at 96°–97° C.

Yield: 80%

EXAMPLE 37

To 2 ml of a solution of 2M of boron trichloride in methylene chloride were added a solution of 0.93 g of aniline in 10 ml of methylene chloride, 1.2 ml of trichloroacetonitrile and 1.2 ml of stannic chloride under ice-cooling. The mixture was refluxed on an oil bath for 24 hr. and poured into a mixture of 16 g of potassium carbonate and 32 ml of methanol under ice-cooling. The mixture was refluxed on an oil bath for 1 hr., filtered to remove the insoluble material and evaporated under reduced pressure. The residue was mixed with water and extracted with ether. The ether layer was washed with dilute HCl, dried over anhydrous magnesium sulfate and evaporated. The residue was purified on a Lobar column. The eluate with 5% ethyl acetate-methylene chloride was evaporated and the residue was recrystallized from ether-petroleum ether to give 0.538 g of anthranilonitrile as crystals melting at 48°–50° C.

Yield: 46%

EXAMPLE 38-46

Using the undermentioned starting material (IIb), the reaction was performed as in Example 37, whereby the corresponding objective compounds (Ib) were obtained. The results were shown in Table 5.

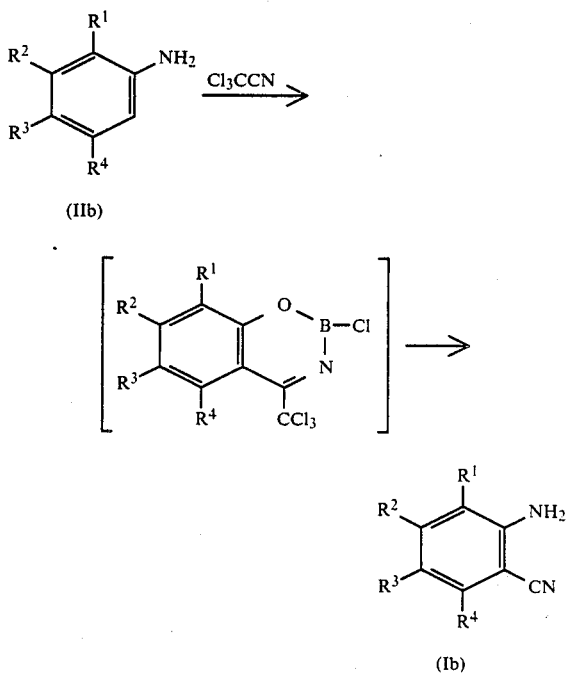

TABLE 5

| Ex. No. | $R^1$ | $R^2$ | $R^3$ | $R^4$ | Solvent | Lewis Acid | Temp. | Time (hr) | m.p. (°C.) | Yield (%) |
|---|---|---|---|---|---|---|---|---|---|---|
| 38 | Cl | H | H | H | DM | $SnCl_4$ | reflux | 24 | 101–102 | 53 |
| 39 | H | Cl | H | H | BN | $SnCl_4$ | reflux | 6 | 163–164 | 54 |
| 40 | H | H | Cl | H | BN | $AlCl_3$ | reflux | 6 | 96–97 | 51 |
| 41 | F | H | H | H | DM | $SnCl_4$ | reflux | 24 | 81–82 | 40 |
| 42 | Me | H | H | H | DM | $SnCl_4$ | reflux | 24 | *1 110–112 | 55 |
| 43 | H | Me | H | H | DM | $SnCl_4$ | reflux | 24 | 94–95 | 48 |
| 44 | H | H | Me | H | BN | $SnCl_4$ | reflux | 6 | 62–63 | 40 |

TABLE 5-continued

| Ex. No. | $R^1$ | $R^2$ | $R^3$ | $R^4$ | Solvent | Lewis Acid | Temp. | Time (hr) | m.p. (°C.) | Yield (%) |
|---|---|---|---|---|---|---|---|---|---|---|
| 45 | H | OMe | H | H | BN | AlCl₃ | room temp. | 4.5 | 94–95 | 55 |
| 46 | H | H | OMe | H | DM | SnCl₄ | reflux | 24 | *²133–141 | 28 |

*¹b.p./1 mmHg
*²HCl—salt

EXAMPLE 47

To a solution of 1.07 g of N-methylaniline in 11 ml of toluene was added 5.5 ml of a solution of 2.02M of boron trichloride in toluene under ice-cooling. The mixture was refluxed on an oil bath for 1 hr. and evaporated under atmospheric pressure to remove the toluene. The residue was mixed with 2 ml of trichloroacetonitrile and heated at 60°–62° C. on an oil bath for 20 hr. The reaction mixture was dissolved in 20 ml of methylene chloride and poured into a mixture of 9.1 g of potassium carbonate and 40 ml of methanol under ice-cooling. The mixture was refluxed on an oil bath for 1 hr., and filtered to remove the insoluble material. The filtrate was evaporated and partitioned between water and methylene chloride. The methylene chloride layer was washed with dilute HCl, dried over anhydrous magnesium sulfate and chromatographed on a column of silica gel (5 g). The eluate with methylene chloride was evaporated and the residue was recrystallized from ether-petroleum ether to give 0.844 g of N-methylanthranilonitrile as crystals melting at 70°–71° C.

Yield: 64%

EXAMPLE 48–49

Using the following starting material (IIb), the reaction was performed as in Example 47, whereby the corresponding objective compounds (Ib) were obtained.

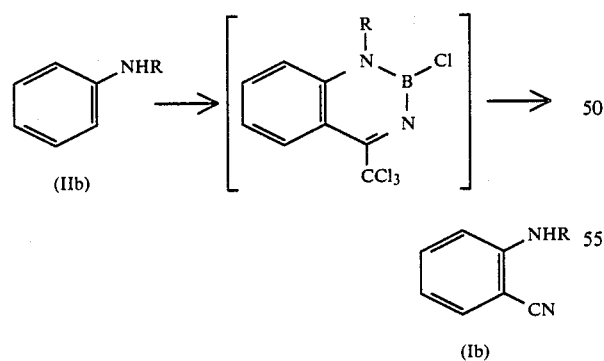

The results were shown in Table 6.

TABLE 6

| Ex. No. | R | Temp. (°C.) | Time (hr) | m.p. (°C.) | Yield (%) |
|---|---|---|---|---|---|
| 48 | CH₂Ph | 80–82 | 20 | 119–120 | 76 |
| 49 | Ph | 80–82 | 20 | 58–59 | 87 |

EXAMPLE 50

To a solution of 10 g of N-(1-benzyl-4-piperidinyl)aniline in 100 ml of 1,2-dichloroethane were added 22.5 ml of a solution of 2M of boron trichloride in 1,2-dichloroethane and 3.1 ml of methyl thiocyanate under ice-cooling and refluxed on an oil bath for 3.5 hr. After ice-cooling, the mixture was mixed with 80 ml of 4N aqueous sodium hydroxide, heated on an oil bath for 1 hr. and evaporated. After cooling, the residue was extracted with benzene, and the benzene layer was dried over anhydrous magnesium sulfate and passed through a column of 100 g of silica gel, eluting with 25% ethyl acetate-benzene. The residue (9.13 g) obtained from the eluate was recrystallized from acetone-ether to give 8.43 g of 2-(1-benzyl-4-piperidinyl)aminobenzonitrile as crystals melting at 104°–105° C.

Yield: 77%

EXAMPLE 51–72

Using the following starting material (IIb), the reaction was performed as in Example 50, whereby the corresponding objective compounds (Ib) and (Ib') were obtained.

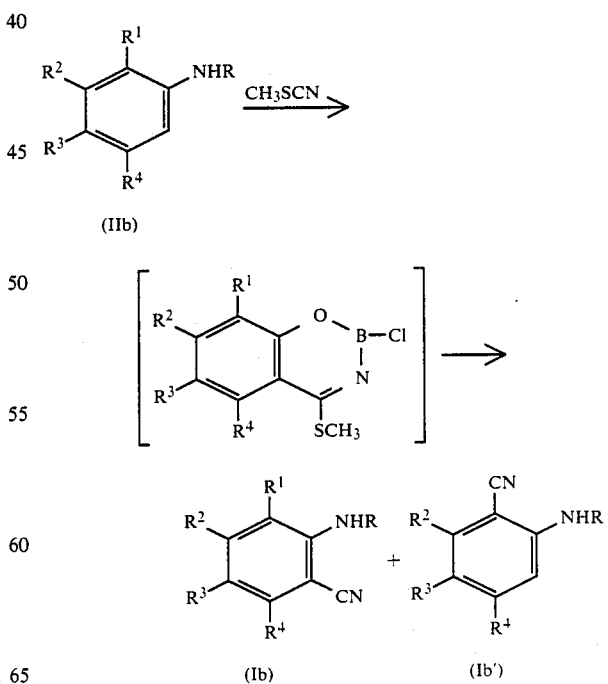

The reaction was performed under refluxing temperature. The results were shown in Table 7.

TABLE 7
| Ex. No. | R¹ | R² | R³ | R⁴ | R | Solvent | Time (hr) | m.p. (°C.) or NMR δ (in CDCl₃) | Yield (%) |
|---|---|---|---|---|---|---|---|---|---|
| 51 | H | H | Cl | H | 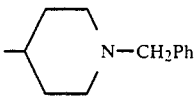 | TL | 2 | 133–134 | 86 |
| 52 | H | Cl | H | H | 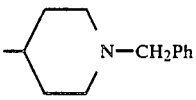 | TL | 3 | 120–121 (4-Cl Compd.)<br>104–106 (6-Cl Compd.) | 51<br>11 |
| 53 | H | H | OMe | H | 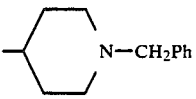 | DE | 1 | 129–130 | 78 |
| 54 | H | OMe | H | H | 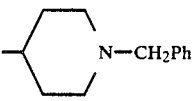 | DI | 4 | 3.78 ppm (4-MeO Compd.) (61%)<br>3.83 ppm (6-MeO Compd.) (39%) | 87 |
| 55 | H | Cl | Cl | H | 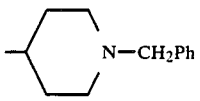 | TL | 4.75 | IR (CHCl₃): 2220 cm⁻¹ | 87 |
| 56 | H | H | H | H | 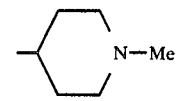 | TL | 2 | 223* | 90 |
| 57 | H | H | Cl | H | 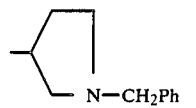 | DE | 6.5 | 206* | 88 |
| 58 | H | H | H | H |  | TL | 2 | 216–218* | 88 |
| 59 | H | Cl | H | H |  | TL | 2 | 224–226* | 81 |
| 60 | H | Cl | Cl | H |  | TL | 2 | 282–283* | 87 |
| 61 | H | H | OMe | H | 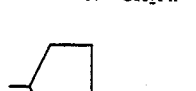 | DE | 4 | 188–189* | 73 |
| 62 | H | OMe | H | H | 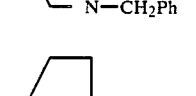 | BN | 4 | 3.72 ppm (4-OMe compd.) (63%)<br>3.77 ppm (6-OMe compd.) (37%) | 76 |
| 63 | H | H | H | H | 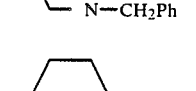 | TL | 5 | 196–197* | 82 |

TABLE 7-continued

| Ex. No. | R¹ | R² | R³ | R⁴ | R | Solvent | Time (hr) | m.p. (°C.) or NMR δ (in CDCl₃) | Yield (%) |
|---|---|---|---|---|---|---|---|---|---|
| 64 | H | H | Cl | H | piperidine-N—CH₂Ph | TL | 6 | 117–118 (d)* | 63 |
| 65 | H | Cl | H | H | piperidine-N—CH₂Ph | TL | 4 | 116–117 (4-Cl compd.)<br>119–121 (6-Cl compd.) | 73<br>5 |
| 66 | H | H | OMe | H | piperidine-N—CH₂Ph | DE | 4.5 | 106–109 (d)* | 80 |
| 67 | H | OMe | H | H | piperidine-N—CH₂Ph | DE | 4.75 | 3.73 ppm (4-OMe compd.) (72%)<br>3.83 ppm (6-OMe compd.) (28%) | 90 |
| 68 | H | H | H | H | —CH₂—pyrrolidine-N—CH₂Ph | TL | 1.5 | 145–146* | 70 |
| 69 | H | H | Cl | H | —CH₂—pyrrolidine-N—CH₂Ph | TL | 4.25 | 196–197* | 63 |
| 70 | H | Cl | H | H | —CH₂—pyrrolidine-N—CH₂Ph | TL | 1 | 210–211 (4-Cl compd.)*<br>188–189 (6-Cl compd.)* | 64<br>10 |
| 71 | H | H | OMe | H | —CH₂—pyrrolidine-N—CH₂Ph | DE | 4.5 | 129–130* | 58 |
| 72 | H | OMe | H | H | —CH₂—pyrrolidine-N—CH₂Ph | DE | 1 | 3.77 ppm (4-OMe compd.) (77%)<br>3.82 ppm (6-OMe compd.) (23%) | 80 |

*HBr salt

EXAMPLE 73

To a solution of 1.19 g of indoline in 10 ml of toluene was added 5.5 ml of a solution of 2.02M of boron trichloride in toluene under ice-cooling, and the mixture was refluxed on an oil bath for 1 hr. and evaporated under atmospheric pressure to remove the solvent. The residue was mixed with 2 ml of trichloroacetonitrile and heated at 60°–62° C. on an oil bath for 20 hr. The product was dissolved in 20 ml of methylene chloride and poured into a mixture of 9.1 g of potassium carbonate and 40 ml of methanol under ice-cooling. The mixture was refluxed on an oil bath for 1 hr. and filtered to remove the insoluble material. The filtrate was evaporated and partitioned between water and methylene chloride. The methylene chloride layer was washed with dilute HCl, dried over anhydrous magnesium sulfate and evaporated to dry- ness. The residue (1.10 g) was purified on a Lobar column and the product (0.913 g) from the methylene chloride eluate was recrystallized from ether-hexane to give 0.836 g of 7-cyanoindoline as crystals melting at 66°–67° C.

Yield: 58%

Anal Calcd (%) for $C_9H_8N_2$: C, 74.97; H, 5.59; N, 19.43; Found (%): C, 74.98; H, 5.60; N, 19.51.

IR (CHCl₃): 3432, 2217 cm⁻¹.

EXAMPLE 74

To a solution of 1.33 g of 1,2,3,4-tetrahydroquinoline in 10 ml of toluene was added 5.5 ml of a solution of 2.02M of boron trichloride in toluene under ice-cooling. The mixture was refluxed on an oil bath for 1 hr. and evaporated under atmospheric pressure to remove the toluene. The residue was mixed with 2 ml of trichloroacetonitrile and heated at 60°–62° C. on an oil bath for 20 hr. The reaction mixture was dissolved in 20 ml of methylene chloride and poured into a mixture of 9.1 g of potassium carbonate and 40 ml of methanol under ice-cooling. The mixture was refluxed on an oil bath for 1 hr. and filtered to remove the insoluble material. The filtrate was concentrated and partitioned between water and methylene chloride. The methylene chloride layer was washed with dilute HCl, dried over anhydrous magnesium sulfate and concentrated to remove the solvent. The residue (1.53 g) was purified on a Lobar column and the product (1.10 g) from the methylene chloride eluate was recrystallized from ether-n-hexane to give 1.07 g of 8-cyano-1,2,3,4-tetrahydroquinoline as crystals melting at 75°–76° C.

Yield: 68%

EXAMPLE 75

To a solution of 0.95 g of N-(1-methyl-4-piperidinyl)aniline in 20 ml of toluene was added 3 ml of a solution of 2M of boron trichloride in toluene under ice-cooling. The mixture was refluxed on an oil bath for 2 hr., mixed with 0.41 ml of methyl thiocyanate and refluxed on an oil bath for 2 hr. The mixture was cooled with ice water, mixed with 18 ml of 2N aqueous sodium carbonate and stirred for 40 min. The organic layer was separated, dried over anhydrous magnesium sulfate, passed through a column of 5 g of activated charcoal and evaporated under reduced pressure to remove the toluene. The residue was purified for many times, whereby 1.17 g of 2-(1-methyl-4-piperidinyl)aminobenzenethiocarboxyimidic acid methyl ester was obtained as pale yellow oil.

Yield: 89%
NMR (CDCl₃), 9.45 (1H, s); 9.09 (1H, d, J=7 Hz); 2.27 (6H, s)

EXAMPLE 76

To 5.5 ml of a solution of 2.02M of boron trichloride in toluene was added a solution of 1.09 g of N-methylaniline in 10 ml of toluene under ice-cooling. The mixture was refluxed on an oil bath for 1 hr. and evaporated under atmospheric pressure. After cooling, the residue was stirred with 1 ml of methyl thiocyanate for 30 min. under ice-cooling and for 2.5 hr. at room temperature. The product was suspended on 10 ml of toluene, mixed with 15 ml of 4N aqueous sodium hydroxide and stirred at 110° C. on an oil bath for 30 min. After cooling, the toluene layer was washed with dilute HCl and then water, dried over anhydrous magnesium sulfate and evaporated in vacuo. The residue was subjected to silica gel chromatography and the eluate with methylene chloride was evaporated and the residue was recrystallized from ether-petroleum ether to give 0.987 g of N-methylanthranilonitrile as white crystals melting at 70°–71° C. Yield: 75%

EXAMPLE 77–82

Using the following starting material (IIb), the reaction was performed as in Example 76, whereby the corresponding objective compounds (Ib) were obtained. The results were shown in Table 8.

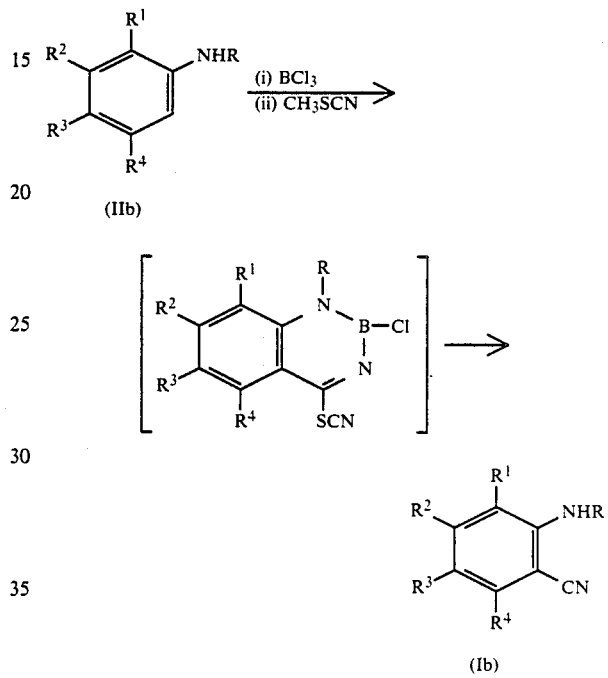

(wherein $R^1$, $R^2$, $R^3$, $R^4$ and R has the same meaning as defined above).

TABLE 8

| Ex. No. | $R^1$ | $R^2$ | $R^3$ | $R^4$ | R | Temp. (°C.) | Time (hr) | m.p. (°C.) or IR (cm$^{-1}$) | Yield (%) |
|---|---|---|---|---|---|---|---|---|---|
| 77 | H | H | H | H | n-Pr | r.t. | 15 | 3370, 2205 | 71 |
| 78 | H | H | H | H | CH₂Ph | r.t. | 15 | 118–120 | 88 |
| 79 | H | F | H | H | Et | r.t. | 24 | 43–48 | 75 |
| 80 | H | H | F | H | Et | r.t. | 65 | 3470, 2205 | 70 |
| 81 | H | OMe | H | H | Et | r.t. | 3 | 77–92 | 78 |
| 82 | H | H | OMe | H | Et | r.t. | 68 | 57–58 | 10 |

Note: r.t. = room temperature

EXAMPLE 83

To 5.5 ml of a solution of 2.02M of boron trichloride in toluene was added a solution of 1.69 g of diphenylamine in 10 ml of toluene under ice-cooling and the mixture was refluxed for 1 hr. on an oil bath. After cooling, 1 ml of methyl thiocyanate was added to the mixture and stirred at room temperature for 5 hr. The reaction mixture was poured into 4N aqueous sodium hydride under ice-cooling and stirred at 110° C. on an oil bath for 30 min. After cooling, the toluene layer was washed with dilute HCl and water, dried over anhydrous magnesium sulfate and evaporated under reduced pressure. The residue was chromatographed on a column of silica gel. The eluate with toluene was evaporated and the residue was recrystallized from ether-petroleum ether as white crystals melting at 58°–59° C.

Yield: 72%

EXAMPLE 84–85

Using the following starting material (IIc), the reaction was performed in the same manner as in Example 83, whereby the corresponding objective compounds (Ic) were obtained. The results were shown in Table 9.

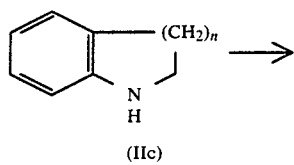

(IIc)

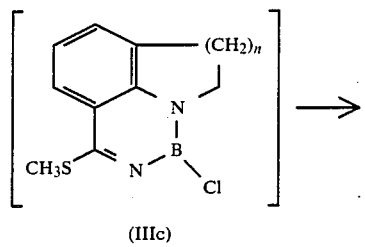

(IIIc)

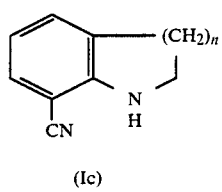

(Ic)

(wherein n is an integer of 1 or 2).

TABLE 9

| Ex. No. | n | Temp (°C.) | Time (hr) | m.p. (°C.) | Yield (%) |
|---|---|---|---|---|---|
| 84 | 1 | r.t. | 3 | 66–67 | 71 |
| 85 | 2 | r.t. | 3 | 75–76 | 74 |

Note: r.t. = room temperature

EXAMPLE 86

To 5.4 ml of a solution of 2.04M of boron trichloride in toluene was added a solution of 1.67 g of carbazole in 10 ml of toluene, and the mixture was refluxed for 1 hr. After cooling, the mixture was treated with 1 ml of methyl thiocyanate and stirred at room temperature for 3 hr. The reaction mixture was poured into 4N aqueous sodium hydroxide under ice-cooling and stirred at 100° C. on an oil bath for 30 min. After cooling, the reaction solution was extracted with methylene chloride, washed with water and dried over anhydrous magnesium sulfate. The residue was chromatographed on a column of silica gel, and the eluate with methylene chloride was discarded. The eluate with 10% acetonitrile-methylene chloride was concentrated, and the product was recrystallized from acetone-ether to give 1.45 g of 1-cyanocarbazole as white crystals melting at 200°–201° C.

Yield: 75%

Anal Calcd (%) for $C_{13}H_8N_2$: C, 81.23; H, 4.20; N, 14.58; Found (%): C, 81.53; H, 4.22; N, 14.52.

EXAMPLE 87

Using the following starting material (IId), the reaction was performed in the same manner as in Example 86, whereby the corresponding objective compounds (Id) were obtained. The results were shown in Table 10.

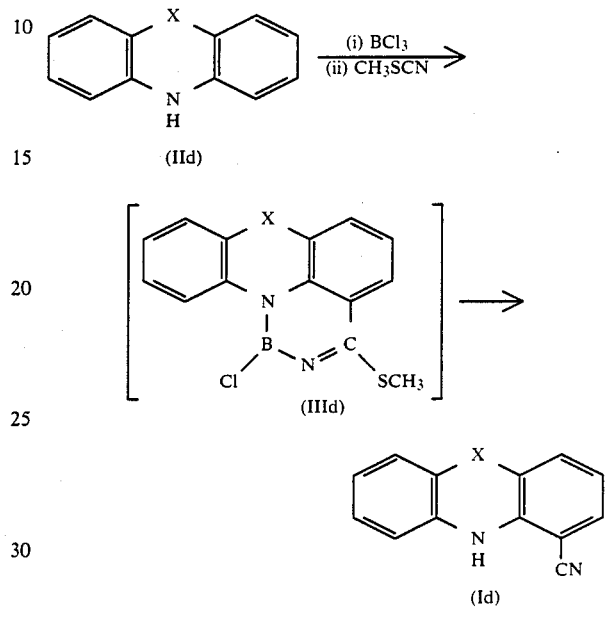

(wherein X has the same meaning as defined above).

TABLE 10

| Ex. No. | X | Temp (°C.) | Time (hr) | m.p. (°C.) | Yield (%) |
|---|---|---|---|---|---|
| 87 | S | r.t. | 2 | 172–173 | 34 |

Note: r.t. = room temperature

EXAMPLE 88

To 5 ml of a solution of 2.02M of boron trichloride in 1,2-dichloroethane was added 1.35 g of 3,4-dihydro-2H-1,4-benzoxazine in 10 ml of 1,2-dichloroethane under ice-cooling, and further a solution of 0.82 ml of methyl thiocyanate and 2.9 ml of n-tributylamine in 10 ml of 1,2-dichloroethane was added dropwise to the mixture within 6 min. After stirring at room temperature for 5 hr., the mixture was poured into 60 ml of saturated aqueous sodium hydrogencarbonate and stirred at 110° C. on an oil bath.

After evaporating 1,2-dichloroethane, the mixture was stirred for 1 hr. at the same temperature. After cooling, the reaction mixture was extracted with toluene, washed with dilute HCl and water and dried over anhydrous magnesium sulfate. Under reduced pressure toluene was evaporated. The residue was chromatographed on a column of silica gel and the eluate with methylene chloride was evaporated and recrystallized from ether—petroleum ether to give 1.17 g of 8-cyano-3,4-dihydro-2H-1,4-benzoxazine as white crystals melting at 79°–80° C.

Yield: 73%

Anal Calcd (%) for $C_9H_8N_2O$: C, 67.48; H, 5.03; N, 17.49; Found (%): C, 67.72; H, 5.16; N, 17.58.

IR (CHCl$_3$): 3430, 2214 cm$^{-1}$.

EXAMPLE 89-90

Using the following starting material (IIc), the reaction was performed in the same manner as in Example 88, whereby the corresponding objective compounds (Ic) were obtained. The results were shown in Table 11.

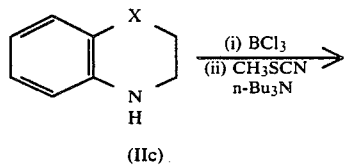

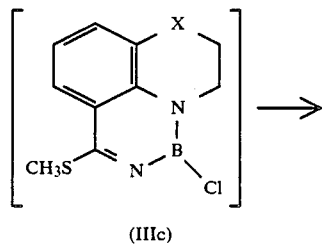

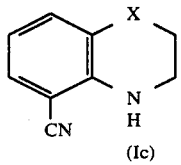

(wherein X has the same meaning as defined above).

TABLE 11

| Ex. No. | X | Temp (°C.) | Time (hr) | m.p. (°C.) | Yield (%) |
|---|---|---|---|---|---|
| 89 | S | r.t. | 5 | 144–145 | 44 |
| 90 | N—Me | r.t. | 17 | 110–111 | 48 |

Note: r.t. = room temperature

What we claim is:

1. A process for the ortho-cyanation of phenols or phenylamines which comprises
reacting a phenyl compound of the formula:

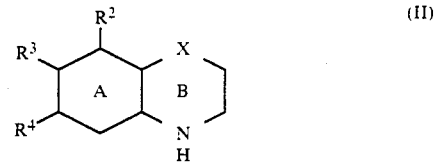

wherein A is a benzene ring, $R^1$, $R^2$, $R^3$ and $R^4$ each is hydrogen, halogen, $C_1$–$C_5$ alkyl, $C_1$–$C_5$ alkoxy, $C_1$–$C_5$ alkylthio, $C_6$–$C_{12}$ aryloxy, $C_7$–$C_{15}$ aralkyl, $C_7$–$C_{15}$ aralkoxy or $C_1$–$C_{10}$ acylamino, or $R^1$ and $R^2$ or $R^2$ and $R^3$ each taken together form a condensed benzene ring optionally substituted by halogen, $C_1$–$C_5$ alkyl or $C_1$–$C_5$ alkoxy, Y is hydroxy, amino or NHR wherein R is $C_1$–$C_5$ alkyl, $C_7$–$C_{15}$ aralkyl, $C_6$–$C_{12}$ aryl, N-(methyl- or benzyl-substituted)aza($C_3$–$C_7$)cycloalkyl or N-(methyl- or benzyl-substituted)aza($C_3$–$C_7$)cycloalkyl-methyl, or R and $R^1$ taken together form a 5- or 6-membered heterocycle of the formula:

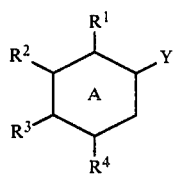

in which X is a single bond, O, S or N(methyl)- and wherein the B ring has optionally a condensed benzene ring or condensed benzene ring optionally substituted by halogen, $C_1$–$C_5$ alkyl or $C_1$–$C_5$ alkoxy attached thereto and wherein the A ring, $R^2$, $R^3$ and $R^4$ are defined above, with $C_1$–$C_5$ alkyl thiocyanate or $C_6$–$C_{12}$ aryl thiocyanate when Y is hydroxy; and with trichloroacetonitrile, $C_1$–$C_5$ alkyl thiocyanate or $C_6$–$C_{12}$ aryl thiocyanate when Y is NHR in the presence of boron trichloride or boron tribromide and treating the resultant product with an alkali.

2. The process according to claim 1, wherein when said trichloroacetonitrile is reacted, the alkali is a weak alkali.

3. The process according to claim 1, wherein when said alkyl or said aryl thiocyanate is reacted, the alkali is a weak alkali or a strong alkali.

4. The process according to claim 2, wherein said weak alkali is sodium hydrogen carbonate, sodium acetate or potassium phosphate.

5. A process according to claim 3, wherein said weak alkali is sodium hydrogen carbonate, sodium acetate or potassium phosphate.

6. A process according to claim 3, wherein said strong alkali is sodium hydroxide or potassium hydroxide.

7. A process according to claim 1, in which said phenyl compound is represented by the formula:

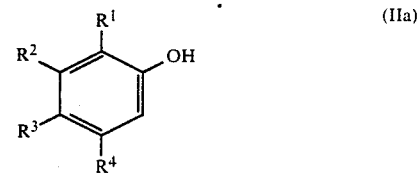

wherein $R^1$, $R^2$, $R^3$ and $R^4$ are as defined above.

8. A process according to claim 1, in which said phenyl compound is represented by the formula:

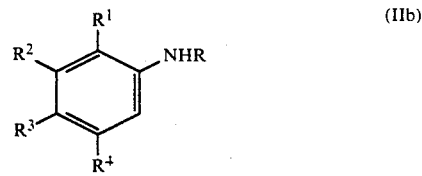

wherein R is $C_1$–$C_5$ alkyl, $C_7$–$C_{15}$ aralkyl, $C_6$–$C_{12}$ aryl, N-(methyl- or benzyl-substituted)aza($C_3$–$C_7$)cycloalkyl or N-(methyl- or benzyl-substituted)aza($C_3$–$C_7$)cycloalkylmethyl and $R^1$, $R^2$, $R^3$ and $R^4$ are as defined above.

9. A process according to claim 1, in which said phenyl compound is represented by the formula:

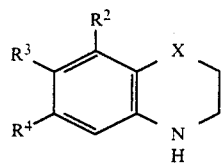

(IIc)

(wherein R², R³, R⁴ and X are as defined above).

10. A process according to claim 1, in which said phenyl compound is represented by the formula:

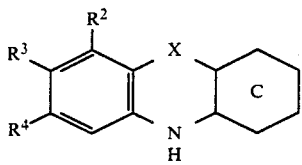

(IId)

(wherein C ring is benzene ring optionally substituted by halogen, $C_1$-$C_5$ alkyl or $C_1$-$C_5$ alkoxy and R², R³, R⁴ and X are as defined above).

11. A process according to claim 7, in which the compound (IIa) is α-naphthol or β-naphthol.

12. A process according to claim 9, in which the compound (IIc) is 1,2,3,4-tetrahydroquinoline, indoline, 2,3-dihydro-4H-1,4-benzothiazine, N-methylbenzopiperazine or 3,4-dihydro-2H-1,4-benzoxazine.

13. A process according to claim 10, in which the compound (IId) is carbazole or phenothiazine.

14. A process according to claim 1, in which the reaction is carried out in the process of a Lewis acid.

15. A process according to claim 7, in which the reaction is carried out via an intermediate of the formula:

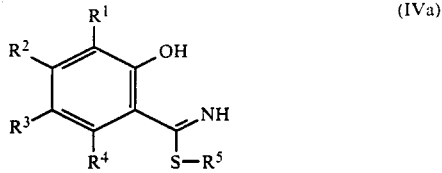

(IVa)

(wherein R⁵ is $C_1$-$C_5$ alkyl and R¹, R², R³ and R⁴ are as defined above).

16. A process according to claim 8, in which the reaction is carried out via an intermediate of the formula:

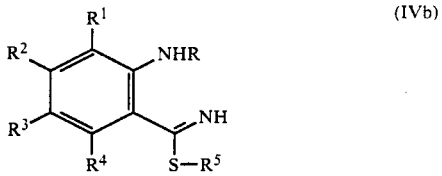

(IVb)

(wherein R⁵ is $C_1$-$C_5$ alkyl and R¹, R², R³ and R⁴ are as defined above).

* * * * *